United States Patent [19]

Irwin

[11] Plant 4,065

[45] June 28, 1977

[54] KALANCHOE PLANT

[76] Inventor: Lawrence T. Irwin, P.O. Box 657, Canyon, Tex. 79015

[21] Appl. No.: 693,880

[22] Filed: June 7, 1976

[51] Int. Cl.[2] ..... A01H 5/00
[52] U.S. Cl. ..... Plt./68
[58] Field of Search ..... Plt./68

*Primary Examiner*—Robert E. Bagwill
*Attorney, Agent, or Firm*—Frank B. Robb

EXEMPLARY CLAIM

1. A new and distinct variety of Kalanchoe plant, substantially as herein shown and described, characterized particularly as to novelty by the unique combination of tall, upright, vigorous growth; earliness of flower; profusion of flowers carried on a sturdy stem well above the foliage; medium to large size flexible foliage of fern green color; the unique mandarin red color of its blooms together with the adaptability of photoperiod manipulation for year round flowering.

1 Drawing Figure

The present invention relates to a new and distinct variety of Kalanchoe Plant which was originated by me by crossing the kalanchoe variety known as "Exotic" (U.S. Plant Pat. No. 3,149) with an unpatented variety known as "Ramona", the former being the seed parent and the latter being the pollen parent.

As a result of this breeding, I have selected a new and improved Kalanchoe variety which is distinguished from its parents, as well as from all other Kalanchoe varieties of which I am aware, as evidenced by the following unique combination of principal characteristics, which are outstanding in the new variety and which make it a valuable addition to the line of Kalanchoe varieties which are presently commercially available:

1. Its vigorous free breaking habit;
2. Its earliness of bloom;
3. Its ability to produce a large pot plant from a single cutting;
4. Its ability to be flowered the year around, and
5. Its unique Mandarin Red Color.

Asexual reproduction of my new Kalanchoe variety by means of cuttings, performed by me in my greenhouse located at Canyon, Texas, shows that the foregoing characteristics and distinctions come true and are established and transmitted through succeeding propagations.

The accompanying drawing shows a typical blooming plant of my new variety, as well as a close-up view of the flowers as depicted in color as nearly true as it is possible to make the same in a color illustration of this character.

The following is a detailed description of my new variety with color terminology in accordance with Maerz and Paul Dictionary of Color as contained in Exotica No. 3 by A. B. Graf, except where general color terms of ordinary dictionary significance are applicable.

Parentage: Seedling.
Seed Parent: "Exotic" (Plant Pat. No. 3,149).
Pollen Parent: "Ramona" (unpatented).
Propagation: Holds its distinguishing characteristics through succeeding propagation by cuttings.
Locality where grown and observed: Canyon, Tex.
Plant:
- *Form.*—Tall; much branched; upright.
- *Growth habit.*—Medium; upright; branching.
- *Rooting habit.*—Coordinate; roots easily from any part of the stem forming a fibrous root system.
- *Blooming habit.*—Natural flowering occurs approximately Dec. 15 as the plant is a short day plant.
- *Blooming season.*—Due to its short day response to flowering, this new variety can be brought into bloom the year round by appropriate photoperiodic manipulation; suitable for forcing and adaptable to year around flowering because of day length manipulation.

Foliage:
- *Size.*—Large.
- *Quantity.*—Abundant.
- *Color.*—New foliage — Upper side — (83) Fern Green; Under side — (83−). Old foliage — Upper side — (83+); Under side — (83).
- *Shape.*—Oval; obtuse.
- *Texture.*—Upper side — Glossy and smooth. Under side — Smooth.

Disease resistance: As compared with other new varieties, it is much more resistant than older standard varieties in comparison with such other varieties grown in the same greenhouses under the same conditions at Canyon, Tex.

Flower: Pistillate; staminate; perfect complete.
- *Size.*—Diameter — 1.8 cm. Depth — 1.2 cm.
- *Petals.*—Length — 0.8 cm. Width — 0.7 cm.
- *Form.*—Perfect complete umbel ovary superior.
- *Color.*—Petals — Upper side — New flowers, Mandarin Red (24); Older flowers, (24−) with lines and specks of (24). Under side — New flowers (29–31) range of color. Throat of corolla — There is no distinct eye.
- *Blooming period.*—From 4 to 5 weeks.

Fruit: None.

Hardiness: Good in range of 50° F to 100° F as grown in the greenhouse.

General observations: This variety has all the characteristics of a good pot plant with vigor, color and upright form which makes it distinctive from all other Kalanchoe varieties.

I claim:

1. A new and distinct variety of Kalanchoe plant, substantially as herein shown and described, characterized particularly as to novelty by the unique combination of tall, upright, vigorous growth; earliness of flower; profusion of flowers carried on a sturdy stem well above the foliage; medium to large size flexible foliage of fern green color; the unique mandarin red color of its blooms together with the adaptability of photoperiod manipulation for year round flowering.

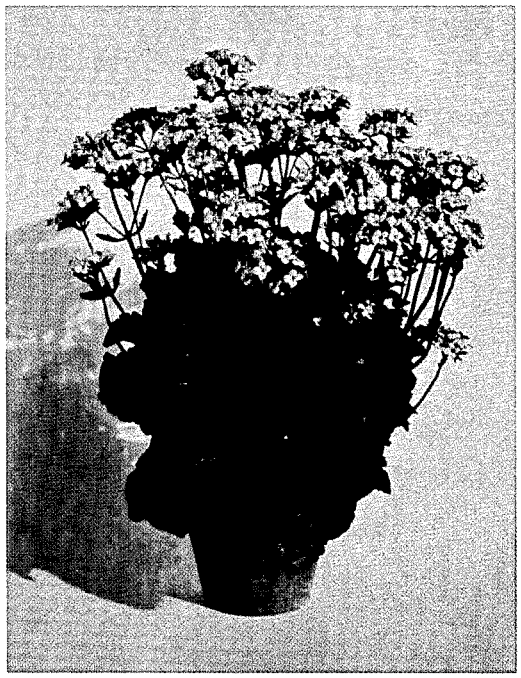
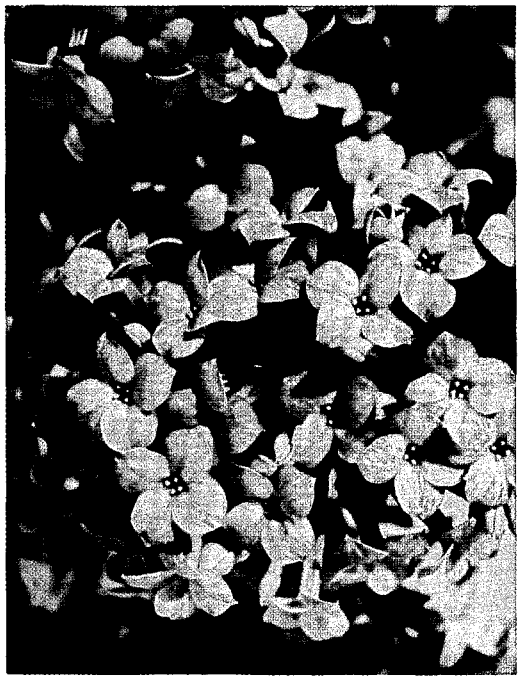

* * * * *